United States Patent [19]

Smalley et al.

[11] Patent Number: 5,137,710
[45] Date of Patent: Aug. 11, 1992

[54] CELL BLOCK PREPARATION

[75] Inventors: Graham M. Smalley, Manchester; Alan Heywood, Warrington, both of England

[73] Assignee: Shandon Scientific Limited, Runcorn, England

[21] Appl. No.: 550,612

[22] Filed: Jul. 10, 1990

[30] Foreign Application Priority Data

Jul. 10, 1989 [GB] United Kingdom ............... 8915759

[51] Int. Cl.$^5$ ................................................ G01N 1/28
[52] U.S. Cl. ........................................ 424/3; 435/960; 436/63
[58] Field of Search .................. 424/3, 2; 435/960; 436/63

[56] References Cited

U.S. PATENT DOCUMENTS 4,647,543  3/1987  Stöcker ............................ 436/174
4,656,047  4/1987  Kok et al. ......................... 427/2

OTHER PUBLICATIONS

Lim et al. *Microencapsulated Islets as Bioartificial Endocrine Pancreas* Science, 210: 908–910 (1980).

Primary Examiner—Glennon H. Hollrah
Assistant Examiner—Brian M. Burn
Attorney, Agent, or Firm—Vaden, Eickenroht, Thompson, Boulware & Feather

[57] ABSTRACT

A method of preparing a cell block for cytological examination of cellular material such as fine needle aspirate material comprises depositing gel medium, preferably an algin medium, and sample material in an enclosure defined by a support web, and then causing the gel medium to set to form a button that can be subjected to processing routines to produce a processed button embeddable in embedding medium. The gel medium and the sample material are preferably codeposited in the enclosure by centrifugation, the support web being prewetted with a setting agent for the gel medium.

A carrier that serves to support the support web during deposition and that is foldable to form a processing cassette for the deposited and set button is also disclosed.

6 Claims, 2 Drawing Sheets

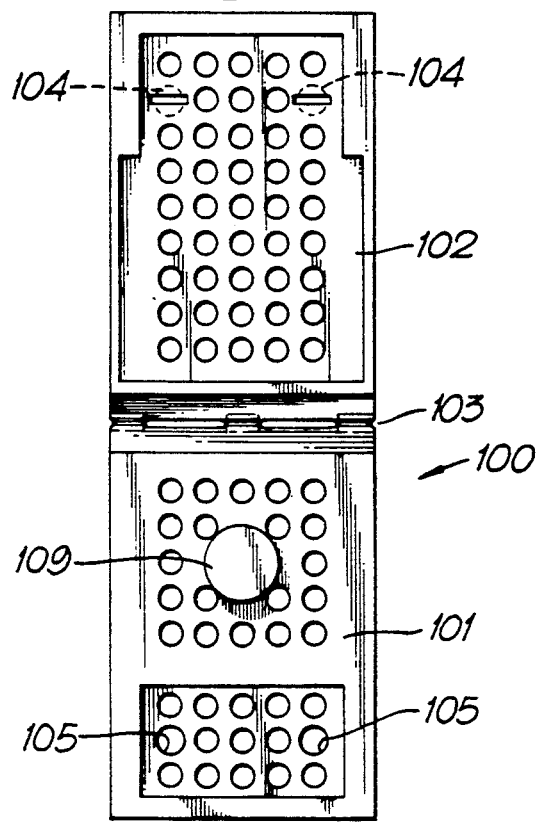
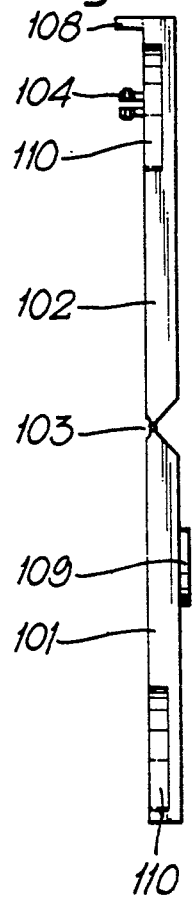
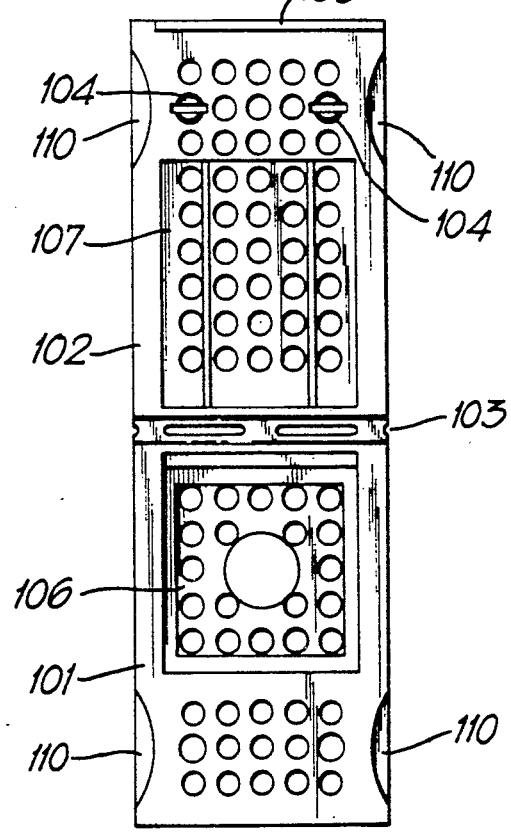

CELL BLOCK PREPARATION

FIELD OF THE INVENTION

The invention concerns cell block preparation for the examination of diagnostic samples, especially fine needle aspirate samples.

BACKGROUND OF THE INVENTION

Fine needle aspiration cytology for the diagnosis of malignancy is a well established procedure. Slide preparations for cytological staining are often made as smears directly from the needle. This technique requires a great deal of expertise and is usually performed by the operating clinician, a cytotechnological or other qualified person. As a consequence, slides received by the laboratory can vary greatly in quality. Cellular damage arising from the method of smearing material onto the slides, unintentional air-drying and poor fixation are common occurences. Furthermore, from a diagnostic standpoint, only small amounts of material are sometimes aspirated from the fibrous tissues (such as breast lumps, from which a large percentage of total aspirates are taken). The cell block technique compensates for many of these disadvantages.

THE PRIOR ART

The cell block technique itself is not new and takes an intermediate position between histological and cytological techniques. Cellular debris and friable tissue fragments are isolated from serous fluids by centrifugation. The sediment may be directly smeared or centrifuged (using a cytocentrifuge such as, for instance, disclosed in EP-A-0,047,840 or EP-A-0,205,106) onto slides for cytological preparations. Alternatively histological preparations may be made from the same sediment (especially if cellular clots and small pieces of tissue are visible) by manually embedding the material into a gelling matrix and processing the resultant cell block into paraffin wax so that thin sections may be taken. The main advantage for the pathologist of the latter technique is that the cells resemble those seen in histology. In order for cell blocks to be prepared from fine needle aspirates (FNA's) the material must be transported to the laboratory in a fluid (preferably a fixative such as neutral buffered formalin).

The use of cell blocks for processing cytology fluids has been reported since 1947 when Chapman and Whalen (N.Eng.J.Med.237:15, 1947) first described the technique for serous fluids. Many methods have since been developed but few have gained universal appeal. Some use agar to bind the sedimented cells and tissue particles (Kung I. T. M., Yuen R. W. S., Acta Cytologica 33:53–60, 1988; Olson N. J. et. al, Acta Cytologica 30:409–412, 1986) but since the agar has to be kept hot, the procedure is also inconvenient. Most methods are time consuming and therefore not practicable on a large number of specimens. Krogerus and Anderson (Acta Cytologica 32:585–587, 1988) for example, have proposed processing sedimented cells into wax without removing the material from the centrifuge tube by re-pelleting the sample and decanting the processing fluid. Elsewhere expensive reagents, as with the thrombin clot method (Karnauchow P. N., Bonin R. E., J. Clin. Path. 35:688, 1982) have probably prevented this otherwise quick technique from becoming established.

The use of algin gel as an entrapment medium to support viable cells has been the subject of a scientific paper, the authors of which have successfully performed histochemical and immunochemical staining procedures on paraffin processed material (Lim F., Sun A. M., Science 210:908–910, 1980).

An object of the present invention is to facilitate the preparation of cell blocks for use in such techniques.

SUMMARY OF THE INVENTION

In one aspect, the invention provides a method of preparing a cell block, comprising depositing sample material and settable gel medium in an enclosure bounded by a support web; causing said gel medium to set to entrap the sample material; and thereafter processing the gel medium and entrapped sample material in the manner of a tissue sample to provide an embeddable button.

The gel medium may be deposited in the enclosure prior to deposition of the sample material but in preferred embodiments of the invention the gel medium and the sample material are codeposited. Deposition of at least the sample material is preferably effected by centrifugation.

Thus in preferred practice, the gel medium and the sample material are codeposited by centrifugation into an enclosure defined by porous web material that can absorb unwanted fluid, e.g. supernatant, in the sample material, using for instance a cytocentrifuge.

Preferably an algin gel medium is used, setting of this being accomplished by contact with a setting agent such as calcium chloride. In preferred practice, the setting agent is applied to the support web so as to initiate setting of the algin gel immediately upon its contacting the support web by deposition in the enclosure.

The invention also consists in apparatus for performing the method, as will be further explained with reference to the accompanying drawings.

BRIEF DESCRIPTION OF THE DRAWINGS

FIGS. 6 to 8 illustrate in rear elevation, side elevation and front elevation, respectively, a preferred form of carrier/processing cassette for practice of the method of the invention.

DESCRIPTION OF PREFERRED EMBODIMENTS

Figure 2:
FIG. 2 illustrates the assembled components of FIG. 1 in a first stage of the method.
Figure 1:
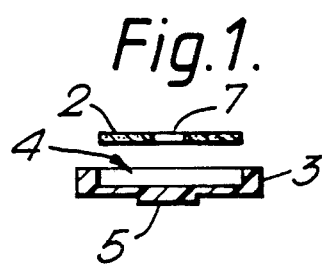
FIG. 1 illustrates in diagrammatic section the components of an enclosure and associated carrier for practice of the method of the invention in a preferred embodiment thereof.

In preferred practice of the method of the invention, an enclosure/carrier assembly 1 (FIG. 2) is assembled by stacking one or more sheets of filter card 2 on a backing layer of filter paper (not shown) in a carrier 3 that provides a recess 4 to contain the stacked sheets, and suitable locating means such as a lug 5 for engaging a slide holder 6 (FIG. 3) of a cytocentrifuge. The card and paper stack conveniently is square in plan, 18×18 mm, the filter card(s) 2 having a circular aperture 7 to define the enclosure. The components of the assembly 1 are shown in FIG. 1, and the assembled components in FIG. 2. Prior to use of this assembly, a setting agent (e.g. calcium chloride 5% solution) is applied to the support web constituted by the stacked card(s) 2 and filter paper backing layer, by any suitable means such as a dropper bottle 8 as shown.

Figure 3:
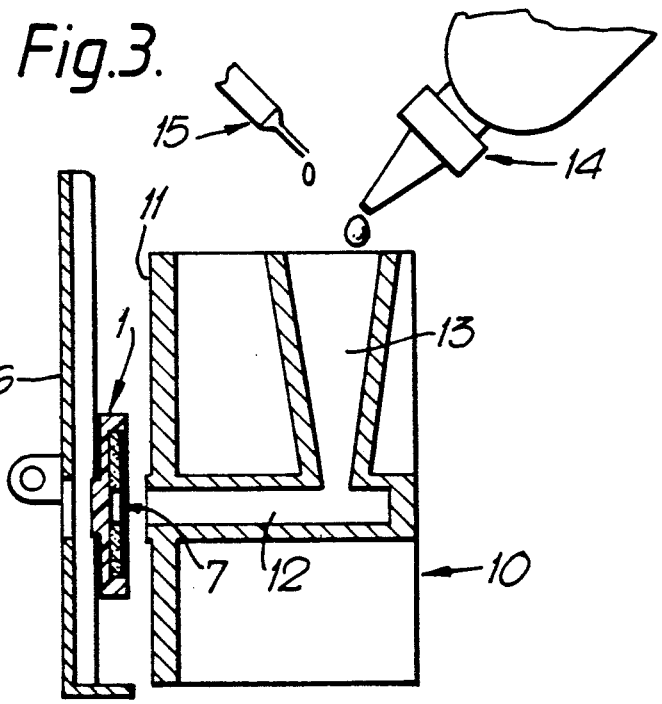
FIG. 3 illustrates, diagrammatically, the preferred codeposition procedure in the method, using a cytocentrifuge as disclosed in EP-A-0,047,840.

The assembly 1 is fitted to the slide holder 6 together with means for codepositing gel medium and sample material into the enclosure. In the illustration of FIG. 3 these means comprise a sample chamber unit 10 generally as disclosed in EP-A-0 047 840 and that has an end flange 11 to be received in the slide holder 6, over the assembly 1, and a sample tube 12 that aligns with the aperture 7 in the filter card(s) 2. Near its (closed) end remote from the flange 11, the sample tube 12 communicates with a funnel tube 13. FIG. 3 shows the described components separated from one another to facilitate understanding of their respective configurations: when fitted together, the lug 5 of the assembly 1 locates in a recess 9 in the slide holder 6 and the flange 11 of the unit 10 engages the assembly 1 to trap it in the holder 6 and to form a sealed connection between the sample tube 12 and the card(s) 2 around the aperture 7 therein. The arrangement is such that when the slide holder 6 with assembly 1 and unit 10 is fitted to a head carrier of the cytocentrifuge (not shown), the slide holder 6 takes up an attitude in which the closed end of the tube 12 is lower than its open end so that material placed in the tube 12 via the funnel tube 13 remains near the closed end of the tube 12.

As indicated in FIG. 3, gel medium and sample material are introduced into the funnel tube 13 from respective applicator devices illustrated diagrammatically at 14 and 15. In preferred practice, the gel medium is the sodium salt of alginic acid in 1% solution, about two drops each of this and of the sample material being placed into the funnel tube 13 by the respective devices 14 and 15.

As explained in EP-A-0 047 840, when the cytocentrifuge is run up, the slide holder 6 tilts to the upright attitude shown in FIG. 3 in which the axis of the tube 12 is horizontal and thus aligned with the artificial gravity vector, so that the gel medium and sample material are codeposited in the enclosure defined by aperture 7. Setting of the gel medium commences when it contacts the setting agent absorbed in the support web structure. Centrifuging is continued to accomplish the required deposition and until the gel medium has set sufficiently to entrap the deposited sample material. Typically the cytocentrifuge would be run up at a low rate to a maximum speed of 1500 rpm, held at that speed for five minutes, and then brought to rest.

Figure 4:
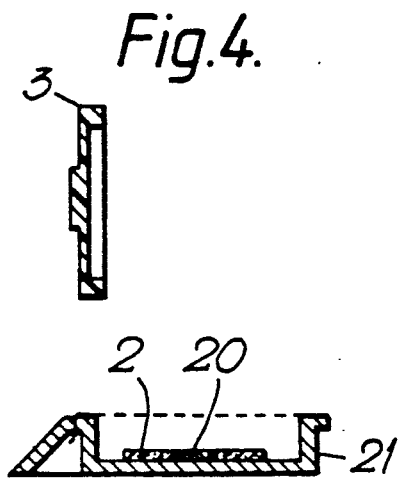
FIG. 4 illustrates transfer of the enclosure with gel/sample button to a processing cassette.
Figure 5:
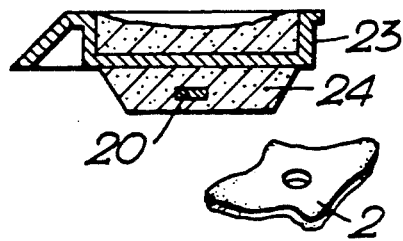
FIG. 5 illustrates a cell block resulting from embedding a processed gel/sample button.

The assembly 1, now containing a gel button 20 (FIG. 4), would then be removed from the slide holder 6. If required, complete setting of the gel medium can now be stimulated by immersion of the support web and gel button in setting agent. This may be accomplished by transferring the web and gel button to a conventional processing cassette the base of which is shown at 21, in FIG. 4, or in a processing cassette constituted by the carrier 3 and a suitable cover, as explained hereafter with reference to FIGS. 6 to 8. When the gel is fully set, the gel button, still in the support web, is subjected to conventional tissue processing or analogous procedures. At the embedding stage, the support web is preferably removed to avoid damage to the microtome blade in subsequent sectioning of the resulting cell block. Embedding is desirably accomplished in an embedding mould (10×10 mm) to produce a cell block 24 attached to a support 23 with the configuration shown in FIG. 5.

In preferred practice the carrier forms part of a processing cassette to minimise handling of and possible damage to the gel button before it is fully set and processed to the point at which it is ready for embedding. FIGS. 6 to 8 illustrate a preferred configuration for a carrier/processing cassette formed as an acetal resin moulding.

As shown in these Figures, the carrier/cassette generally referenced 100 comprises two parts 101, 102 united by an integral hinge portion 103 so that the part 102 can be folded over the part 101, the part 102 having snap-catch pegs 104 that engage in holes 105 in the part 101 to secure the part 102 in place over the part 101 and thereby form a processing cassette.

The part 101 serves as the carrier in the described method of the invention and for this purpose has a square recess 106, 18 mm×18 mm, in its front face to receive the card and paper stack of the support web described. The part 102 forms a cover when folded over the part 101 and has a recess 107 in its front face to provide clearance over the support web and gel button when the cassette is closed. The recess 107 also accommodates an extension of the filter paper that defines the bottom of the enclosure in the support web.

To assist in securing the part 102 in position over the part 101 in the cassette-forming configuration of the device 100, the end of the part 102 has a forwardly-projecting flange 108 that engages over the corresponding end of the part 101. This serves to maintain alignment should the hinge 103 fracture in handling before processing is complete.

The rear face of the part 101 has a projecting lug 109 for locating the device in a slide holder 6 of a cytocentrifuge in the manner described with reference to FIG. 3. For convenience in opening the cassette after processing is complete, the parts 101, 102 have edge recesses 110 to admit a finger nail. The device 100 is liberally apertured as shown to provide for free flow of processing fluids when in use as a processing cassette.

Reverting to the method of the invention, approximately sixty sections of 5 μm thickness may be cut by microtomy from a cell block such as the block 24 produced in the manner described, and up to six sections can be fitted onto a standard microscope slide for staining with, for example, haematoxylin and eosin. Staining of the gel with Shandon haematoxylin (Activity 2) and also with aqueous alcian blue dye solutions is quite moderate; Mayers haematoxylin on the other hand barely stains the gel at all. Where gel staining is undesirable the material may be removed by treating slides with phosphate buffered saline for approximately 5 minutes before staining: a small percentage of cells may be unavoidably lost during this treatment, though this can be compensated for by taking multiple sections per slide.

The filter paper backing layer of the enclosure has not been illustrated. It may conform in size to the filter card(s) 2 or, as discussed in connection with FIGS. 6 to 8, it may be larger and arranged to project from the assembly 1 on at least one side to provide a convenient "tag" for handling purposes. When the backing layer is larger than the card(s) 2, the excess may be folded over the card(s) on removal from the carrier 3 to protect the partly set gel button from damage or disturbance in subsequent handling and processing.

In routine laboratory practice it is expected that batches of gel buttons would be processed overnight by automated tissue-processing equipment. Storage of cassetted gel buttons after setting and before processing may be accomplished by holding in a pot of 10% formal saline (4% formaldehyde).

Certain sample materials may require pretreatment before the steps described above are carried out. For instance, cytology materials received fresh or in isotonic saline would need pretreatment such as centrifugation (3000 rpm for five minutes) to deposit solids; then decant off supernatant; thereafter resuspend solids, e.g. in 10-15 ml 10% neutral buffered formalin (NBF) (4% formaldehyde). (For heavy sediments or for those containing a visible buffy layer a restricted sample consisting of 3-4 drops of sample transferred to the 10-15 ml of NBF is recommended). After allowing 15-30 minutes for fixation, further centrifugation (3000 rpm for five minutes), decantation and resuspension in approximately 3-4 drops of 10% NBF would provide a sample material appropriate for carrying out the procedures described with reference to the drawing.

Cytology material received in an alcoholic fluid (e.g. Saccomano's fluid) will display an alcohol fixation picture, such as cellular shrinkage and precipitated chromatin. Such material would not require further fixation and its pretreatment could consist simply of centrifugation, decantation of supernatent and resuspension in 10% NBF to provide a low volume sample for the described procedures. Similar pretreatment would be applicable to material received fixed in formaldehyde solutions.

Although very stable to most organic solvents and even to hot wax, the preferred algin gels are, however, very slowly depolymerized by chelating agents such as EDTA, and in the presence of phosphate ions, as in neutral buffered formalin. Cell blocks may nevertheless be prepared from specimens received in neutral buffered formalin, however, because an excess of calcium ions exists in the filter card and paper, effectively mopping up the relatively small amounts of phosphate ions present in a few drops of sample. It is important though that specimens are adequately fixed prior to cell blocks being made. If fixation is used as part of the processing cycle it is suggested that unbuffered formal saline be used or that cell buttons be added directly to the alcohols after the fixation step. The cell button once set nonetheless can withstand a short time in neutral buffered formalin at room temperature without adverse effect. At present the best estimate for stability in neutral buffered formalin is 30 minutes.

Fine needle aspirates may be derived from many tissue sites that can be reached by an 18-22 gauge needle. Most typically these include breast, thyroid and lymph nodes as swelling of these tissues can readily be seen or felt. This 'non-invasive' technique can lead to surgical biopsy or excision of the tissue. So long as the FNA sample is collected in a transport material (fixative or normal saline) cell blocks may be prepared.

It may be possible to prepare cell blocks from other cytological specimens such as bronchial washings, pleural effusions and possibly urines. In such instances the sample should be pre-centrifuged and fixed prior to cell block preparation.

Pellets for Electron Microscopy techniques are formed by centrifugation of fixed particulate specimens such as bacteria, single cells and protozoa. An application may thus be found in EM laboratories, depending on the compatibility of the gel with EM processing fluids and the interaction of calcium ions with the electron beam.

The method of the invention for preparing cell blocks offers the user further advantages over traditional techniques. Firstly the cytocentrifuge used in the preferred technique enables reproducible, standardised cell blocks to be made by significantly reducing operator interference and by defining sample volumes.

Secondly, the preferred algin gel medium is chemically set very efficiently by calcium chloride so that the inconvenience of agar may be avoided. The raw materials are considerably cheaper than thrombin, can be used more readily and do not need to be stored in a refrigerator. For increased shelf life, algin solutions may even be made in formaldehyde-containing solutions.

Thirdly, unlike traditional methods, the preferred algin gel may be easily removed from sections prior to staining without significantly reducing the number of cells available per slide. The mauve staining of the gel after staining with haematoxylin and eosin however, can aid location of a poorly cellular preparation.

We claim:

1. A method of preparing a cell block, characterised by depositing sample material and settable gel medium in an enclosure bounded by a porous support web; causing said gel medium to set to entrap the sample material to form a gel button; and thereafter processing the gel button in the manner of a tissue sample to provide an embeddable button.

2. The method of claim 1 in which said gel medium and said sample material are codeposited in said enclosure.

3. The method of claim 1 in which at least the sample material is deposited in said enclosure by centrifugation.

4. The method of claim 3 in which said gel medium and said sample material are codeposited by centrifugation.

5. The method of claim 4 in which said porous support web is pre-impregnated with setting agent for the gel medium.

6. A method of the character defined in claim 1, wherein
the gel button is enclosed in the support web during processing.

* * * * *